US008755876B2

(12) United States Patent
Chon et al.

(10) Patent No.: US 8,755,876 B2
(45) Date of Patent: Jun. 17, 2014

(54) METHODS AND SYSTEMS FOR ATRIAL FIBRILLATION DETECTION

(71) Applicants: Ki H. Chon, Worcester, MA (US); Jinseok Lee, Worcester, MA (US)

(72) Inventors: Ki H. Chon, Worcester, MA (US); Jinseok Lee, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 13/684,979

(22) Filed: Nov. 26, 2012

(65) Prior Publication Data

US 2013/0144180 A1    Jun. 6, 2013

Related U.S. Application Data

(60) Provisional application No. 61/566,329, filed on Dec. 2, 2011.

(51) Int. Cl.
A61B 5/046    (2006.01)

(52) U.S. Cl.
USPC .......................................................... 600/518

(58) Field of Classification Search
None
See application file for complete search history.

(56) References Cited

U.S. PATENT DOCUMENTS

2007/0032733 A1    2/2007    Burton
2009/0112110 A1*   4/2009    Zhang ........................... 600/518
2009/0318983 A1    12/2009   Armoundas et al.
2010/0016739 A1    1/2010    Shelley et al.
2011/0166466 A1    7/2011    Chon et al.

FOREIGN PATENT DOCUMENTS

| JP | 2005-521532 A | 7/2005 |
| JP | 2007-516024 A | 6/2007 |
| JP | 2009-520568 A | 5/2009 |
| WO | 2012051320 A1 | 4/2012 |
| WO | 2012100175 A1 | 7/2012 |

OTHER PUBLICATIONS

Zhao, H. et al., "Estimation of time-varying coherence function using time-varying transfer functions," Ann Biomed Eng, vol. 33, No. 11, pp. 1582-1594, Nov. 2005.
Zou, R. et al., "A robust time-varying identification algorithm using basis functions," Ann Biomed Eng, vol. 31, No. 7, pp. 840-853, Jul.-Aug. 2003.
Dash, S. et al., "Automatic real time detection of atrial fibrillation," Ann Biomed Eng, vol. 37, No. 9, pp. 1701-1709, Sep. 2009.
Lake, D. E., "Accurate estimation of entropy in very short physiological time series: the problem of atrial fibrillation detection in implanted ventricular devices," Am J Physiol Heart Circ Physiol, vol. 300, No. 1, pp. H319-H325, Jan. 2011.
Tateno, K. et al., "Automatic detection of atrial fibrillation using the coefficient of variation and density histograms of RR and deltaRR intervals," Med Biol Eng Comput, vol. 39, No. 6, pp. 664-671, Nov. 2001.

(Continued)

*Primary Examiner* — Carl H Layno
*Assistant Examiner* — Paula J Stice
(74) *Attorney, Agent, or Firm* — Burns & Levinson LLP; Jacob N. Erlich; Orlando Lopez

(57) ABSTRACT

Methods and systems for automatic detection of Atrial Fibrillation (AF) are disclosed. The methods and systems use time-varying coherence functions (TVCF) to detect AF. The TVCF is estimated by the multiplication of two time-varying transfer functions (TVTFs).

16 Claims, 13 Drawing Sheets

(56) References Cited

OTHER PUBLICATIONS

Huang, C. et al., "A novel method for detection of the transition between atrial fibrillation and sinus rhythm," IEEE Trans Biomed Eng, vol. 58, No. 4, pp. 1113-1119, Apr. 2011.

Kikillus, N. et al., "Three different algorithms for identifying patients suffering from atrial fibrillation during atrial fibrillation free phases of the ECG," Comput. Cardiol., vol. 34, pp. 801-804, 2007.

Scully, C. G. et al., "Physiological Parameter Monitoring from Optical Recordings with a Mobile Phone," IEEE Trans Biomed Eng, Jul. 29, 2011.

Ropella, K. M. "Frequency domain analysis of endocardial signals," Ann. lst. Supers. Sanita, 37(3), 2001, 351-359.

Lee, J. "Atrial Fibrillation Detection using Time-Varying Coherence Function and Shannon Entropy," 33rd Ann. Int'l. Conf. IEEE EMBS (2011), 4685-4688.

International Search Report dated Feb. 6, 2013 for International Patent Application No. PCT/US2012/066626.

Written Opinion dated Feb. 6, 2013 for International Patent Application No. PCT/US2012/066626.

Pearson, S. et al., "Amplitude Modulated Coherence Analysis of Biomedical Signals." Proceedings of the International Workshop on Biosignal Interpretation, vol. 5 (2005): 135-138.

Lee, Jinseok, et al., "An Autoregressive Model-Based Particle Filtering Algorithms for Extraction of Respiratory Rates as High as 90 Breaths Per Minute From Pulse Oximeter." IEEE Transactions on Biomedical Engineering, vol. 57, No. 9: 2158-2167.

* cited by examiner

Fig. 12 seg = 128

| (p,q) | Accuracy | Sensitivity | Specificity | $TH_{ACC}$ | $TH_{SE}$ |
|---|---|---|---|---|---|
| (2,2) | 0.9709 | 0.9718 | 0.9705 | 0.0230 | 0.795 |
| (3,3) | 0.9779 | 0.9795 | 0.9766 | 0.0200 | 0.790 |
| (4,4) | 0.9782 | 0.9833 | 0.9744 | 0.0160 | 0.790 |
| (5,5) | 0.9791 | 0.9822 | 0.9768 | 0.0190 | 0.790 |
| (6,6) | 0.9790 | 0.9850 | 0.9746 | 0.0160 | 0.790 |
| (7,7) | 0.9787 | 0.9848 | 0.9742 | 0.0150 | 0.790 |
| (8,8) | 0.9791 | 0.9815 | 0.9774 | 0.0220 | 0.790 |
| (9,9) | 0.9788 | 0.9815 | 0.9768 | 0.0210 | 0.790 |
| (10,10) | 0.9787 | 0.9833 | 0.9750 | 0.0170 | 0.790 | seg = 96

| (p,q) | Accuracy | Sensitivity | Specificity | $TH_{ACC}$ | $TH_{SE}$ |
|---|---|---|---|---|---|
| (2,2) | 0.9719 | 0.9781 | 0.9672 | 0.1244 | 0.755 |
| (3,3) | 0.9765 | 0.9834 | 0.9711 | 0.0842 | 0.750 |
| (4,4) | 0.9768 | 0.9789 | 0.9753 | 0.1316 | 0.750 |
| (5,5) | 0.9769 | 0.9857 | 0.9703 | 0.0718 | 0.750 |
| (6,6) | 0.9781 | 0.9858 | 0.9724 | 0.0944 | 0.750 |
| (7,7) | 0.9770 | 0.9836 | 0.9721 | 0.1018 | 0.750 |
| (8,8) | 0.9782 | 0.9848 | 0.9733 | 0.1036 | 0.750 |
| (9,9) | 0.9774 | 0.9865 | 0.9707 | 0.0784 | 0.750 |
| (10,10) | 0.9780 | 0.9842 | 0.9734 | 0.1039 | 0.750 | seg = 64

| (p,q) | Accuracy | Sensitivity | Specificity | $TH_{ACC}$ | $TH_{SE}$ |
|---|---|---|---|---|---|
| (2,2) | 0.9695 | 0.9678 | 0.9708 | 0.0100 | 0.714 |
| (3,3) | 0.9715 | 0.9636 | 0.9774 | 0.0100 | 0.710 |
| (4,4) | 0.9719 | 0.9654 | 0.9767 | 0.0100 | 0.710 |
| (5,5) | 0.9711 | 0.9628 | 0.9771 | 0.0100 | 0.712 |
| (6,6) | 0.9713 | 0.9646 | 0.9763 | 0.0100 | 0.710 |
| (7,7) | 0.9714 | 0.9645 | 0.9765 | 0.0100 | 0.710 |
| (8,8) | 0.9717 | 0.9649 | 0.9767 | 0.0100 | 0.710 |
| (9,9) | 0.9706 | 0.9629 | 0.9763 | 0.0100 | 0.708 |
| (10,10) | 0.9695 | 0.9591 | 0.9771 | 0.0100 | 0.710 | seg = 32

| (p,q) | Accuracy | Sensitivity | Specificity | $TH_{ACC}$ | $TH_{SE}$ |
|---|---|---|---|---|---|
| (2,2) | 0.9614 | 0.9697 | 0.9553 | 0.0015 | 0.590 |
| (3,3) | 0.9637 | 0.9668 | 0.9614 | 0.0010 | 0.590 |
| (4,4) | 0.9635 | 0.9704 | 0.9584 | 0.0009 | 0.590 |
| (5,5) | 0.9629 | 0.9699 | 0.9577 | 0.0007 | 0.590 |
| (6,6) | 0.9607 | 0.9629 | 0.9590 | 0.0010 | 0.590 | seg = 16

| (p,q) | Accuracy | Sensitivity | Specificity | $TH_{ACC}$ | $TH_{SE}$ |
|---|---|---|---|---|---|
| (2,2) | 0.9421 | 0.9481 | 0.9377 | 0.00033 | 0.480 |
| (3,3) | 0.9382 | 0.9381 | 0.9383 | 0.00017 | 0.480 |
| (4,4) | 0.9323 | 0.9465 | 0.9218 | 0.00016 | 0.480 | seg = 12

| (p,q) | Accuracy | Sensitivity | Specificity | $TH_{ACC}$ | $TH_{SE}$ |
|---|---|---|---|---|---|
| (2,2) | 0.9222 | 0.9474 | 0.9036 | 0.000076 | 0.380 |
| (3,3) | 0.9021 | 0.8927 | 0.9091 | 0.000036 | 0.390 |
| (4,4) | 0.9053 | 0.9114 | 0.9008 | 0.000046 | 0.400 |

FV-TVCF WITH SE BASED ACCURACY, SENSITIVITY AND SPECIFICITY ARE LISTED WITH OPTIMUM THRESHOLD VALUES

METHODS AND SYSTEMS FOR ATRIAL FIBRILLATION DETECTION

STATEMENT REGARDING FEDERALLY SPONSORED RESEARCH OR DEVELOPMENT

This work was funded in part by the Office of Naval Research, Work Unit N00014-10-1-0640. The U.S. Government has certain rights in the invention.

CROSS REFERENCE TO RELATED APPLICATIONS

This application claims priority U.S. Provisional Application Ser. No. 61/566,329, filed Dec. 2, 2011, entitled TIME-VARYING COHERENCE FUNCTION FOR ATRIAL FIBRILLATION DETECTION, which is incorporated by reference herein in its entirety for all purposes.

BACKGROUND OF THE INVENTION

Atrial fibrillation is the most common sustained dysrhythmia worldwide. Over 2.3 million Americans are currently diagnosed, and the prevalence of AF is increasing with the aging of the U.S. population. Through its association with increased risk for heart failure, stroke and mortality, AF has a profound impact on the longevity and quality of life of a growing number of people. Although new AF treatment strategies have emerged over the last decade, a major challenge facing clinicians and researchers is the paroxysmal nature of AF, which makes it difficult to detect because it is short lasting, often asymptomatic, and intermittent. Thus, there is a pressing need to develop methods for accurate AF detection including paroxysmal rhythms. Such a method would have important clinical applications for pre- and post-treatment detection of AF. For these reasons, the importance of developing new AF detection technologies has been emphasized.

Many algorithms have been developed to detect AF and can be categorized as being based on 1) P-wave detection or 2) RR interval (RRI) variability. AF detection based on P-wave absence has not gained wide acceptance because determination of the P-wave fiducial point localization is challenging, especially for Holter monitoring applications. Indeed, for Holter monitoring, it is difficult to find uncontaminated RR intervals due to motion and noise artifacts which can confound the accuracy of P-wave detection. Subsequently, many studies have used variability of RR interval time series instead. Specifically, the aim is to quantify markedly increased beat-to-beat variability RR interval time series in AF. Consequently, most algorithms show higher sensitivity and specificity values than the methods that screen for the absence of P-waves. However, most of these RR intervals methods are based on comparing the density histogram of the data segment with previously-compiled standard density histograms of RR segments during AF using the Kolmogorov-Smirnov test. The main disadvantage of this approach is that it requires storage of large amounts of histogram data and threshold values of various characteristics of AF.

Accordingly, there is a need for improved methods and systems for detecting atrial fibrillation.

SUMMARY OF THE INVENTION

Methods and systems for automatic detection of Atrial Fibrillation (AF) are disclosed.

In one or more embodiments of the methods and systems of these teachings for detection of Atrial Fibrillation (AF), the methods and systems use time-varying coherence functions (TVCF) to detect AF. The TVCF is estimated by the multiplication of two time-varying transfer functions (TVTFs). The two TVTFs are obtained using two adjacent data segments, each adjacent data segment being a data segment related to R-R intervals, with one data segment as the input signal and the other data segment as the output to produce the first TVTF; the second TVTF is produced by reversing the input and output signals. In order to detect AF, it is determined whether the time-varying coherence function (TVCF) is less than a predetermined quantity.

In one or more embodiments of the system of these teachings, the system includes an analysis component performing the above disclosed determination. Embodiments of computer readable media having computer readable code that causes the one or more processors to perform the above disclosed determination are also disclosed.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that offer any or all advantages or solve any or all state of the art problems.

BRIEF DESCRIPTION OF THE DRAWINGS

The present disclosure is illustratively shown and described in reference to the accompanying drawing in which:

FIG. 12 is a table illustrating FV-TVCF with SE based accuracy.

DETAILED DESCRIPTION

The following detailed description is of the best currently contemplated modes of carrying out these teachings. The description is not to be taken in a limiting sense, but is made merely for the purpose of illustrating the general principles of these teachings, since the scope of these teachings is best defined by the appended claims. Although the teachings have been described with respect to various embodiments, it should be realized these teachings are also capable of a wide variety of further and other embodiments within the spirit and scope of the appended claims.

The present teachings will be more completely understood through the following description, which should be read in conjunction with the drawings. In this description, like numbers refer to similar elements within various embodiments of the present disclosure. Within this description, the claims will be explained with respect to embodiments. The skilled artisan will readily appreciate that the methods, apparatus and systems described herein are merely exemplary and that variations can be made without departing from the spirit and scope of the disclosure.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about."

The following configuration description is presented for illustrative purposes only. Any computer configuration and architecture satisfying the speed and interface requirements may be suitable for implementing the system and method of the present embodiments.

Figure 1:
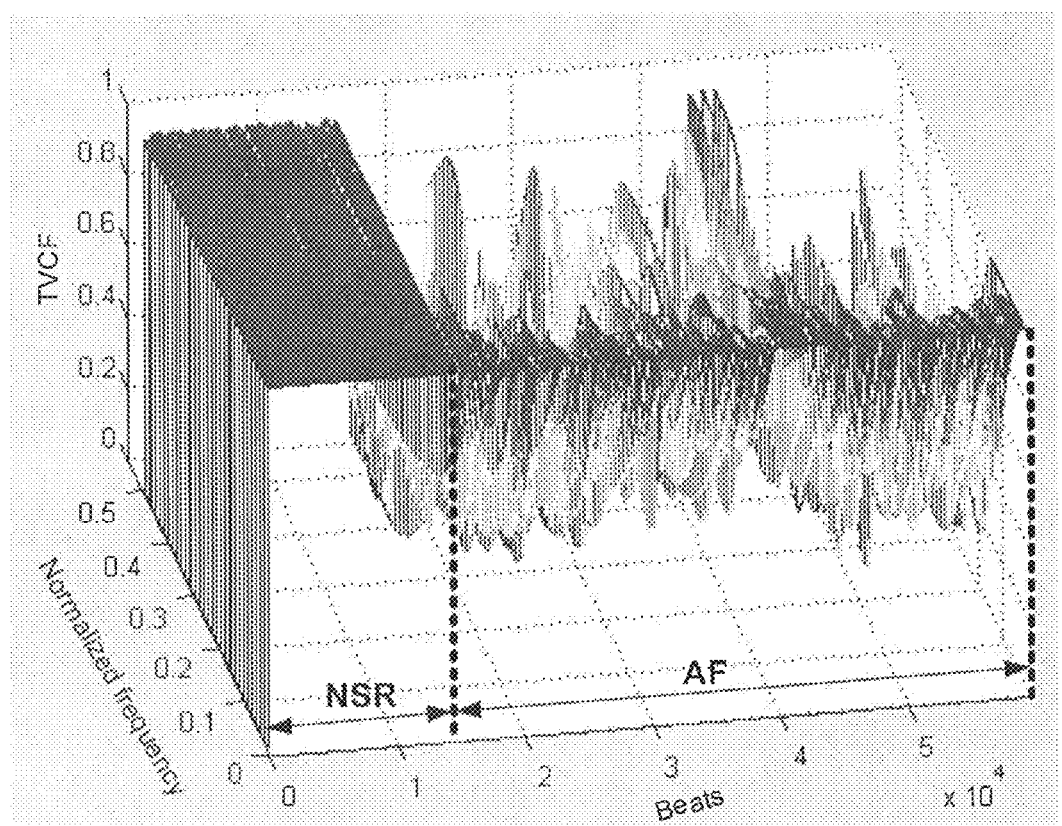
FIG. 1 illustrates a plot of a resultant Time-Varying Coherence Function (TVCF) of subject 8455 of the MIT-BIH AF database according to each beat and normalized frequency.
Figure 1A:
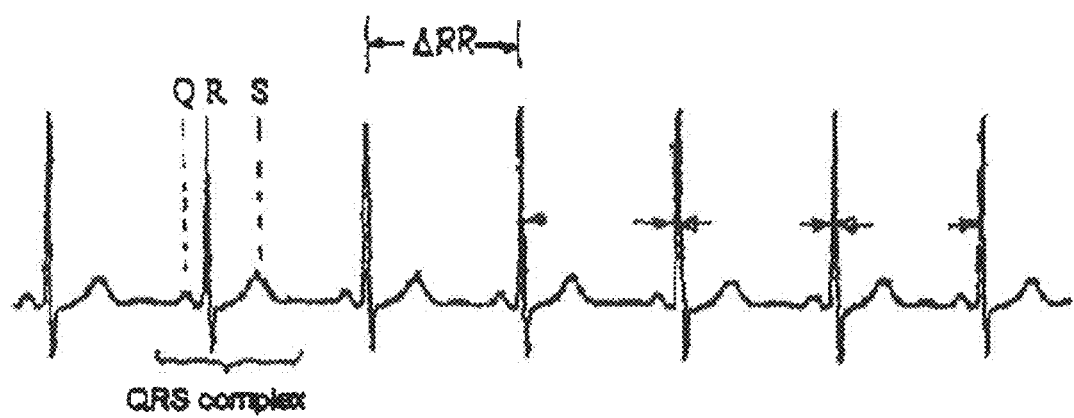
FIG. 1a illustrates the conventional signal obtained from an EKG.

To assist in the understanding of the present teachings the following definitions are presented:

"R-R interval," as used herein, refers to the interval from the peak of one group in an electrocardiogram (EKG) (referred to as a QRS complex) to the peak of the next group in the EKG, as shown in FIG. 1a;

"Sinus Rhythms," as used herein, refers variations of the R-R interval;

"Signals (or data segments) related to R-R intervals," as used herein, refers to signals from which the R-R interval could be derived and which contain the same information; for example, R-R interval time series can be derived from heart rate, pulse rate, blood pressure time variation and photoplethysmographic (PPG) output; obtaining an EKG waveform from a patient is much more complex and difficult then obtaining any of the above.

Method and systems for automatic detection of Atrial Fibrillation (AF) using time-varying coherence functions (TVCF) are disclosed herein. In one or more embodiments, a time-varying coherence function (TVCF) approach is used to discriminate between AF and nonfibrillatory cardiac rhythms.

Figure 9:
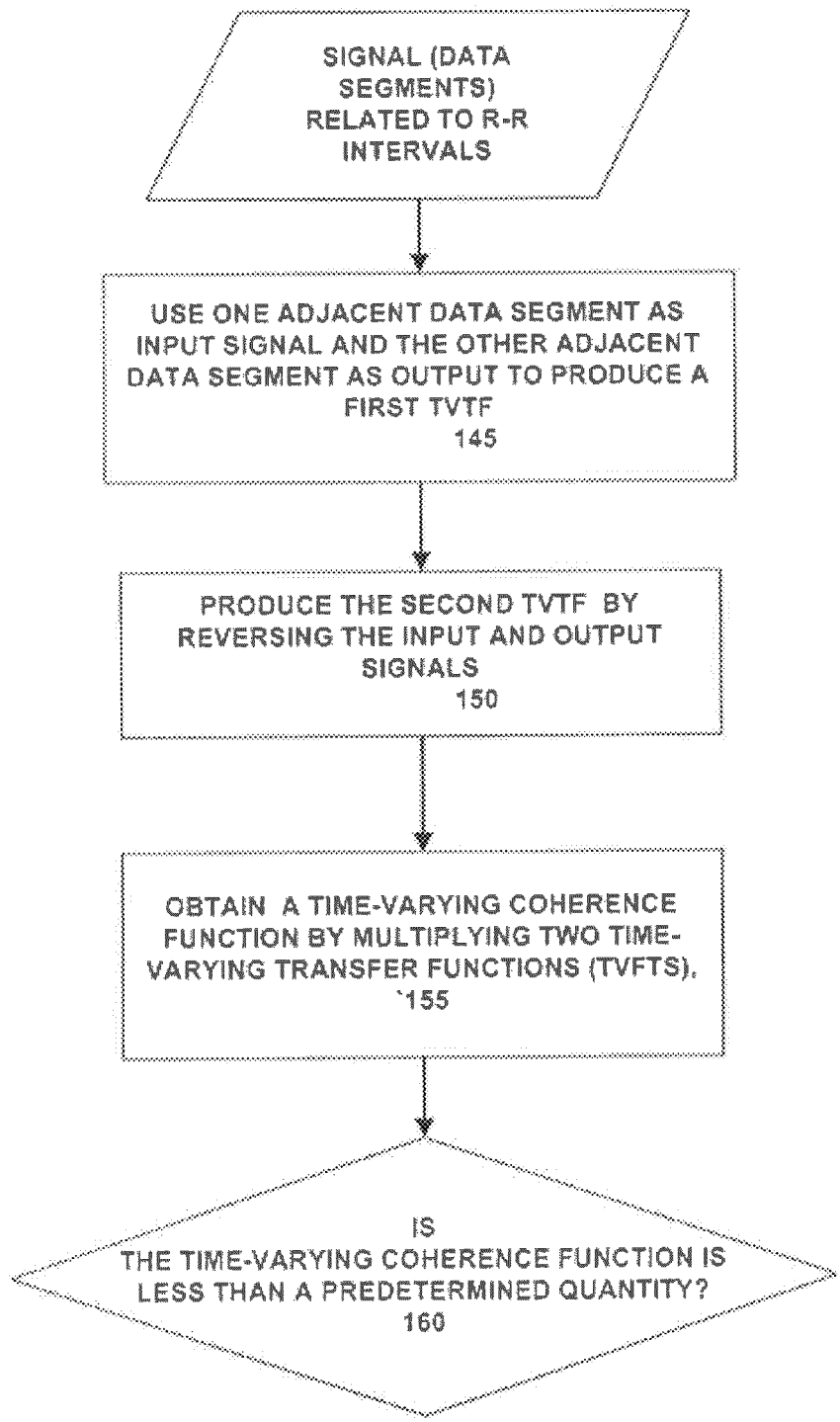
FIGS. 9-11 are flowchart representations of embodiments of the method of these teachings.
Figure 10:
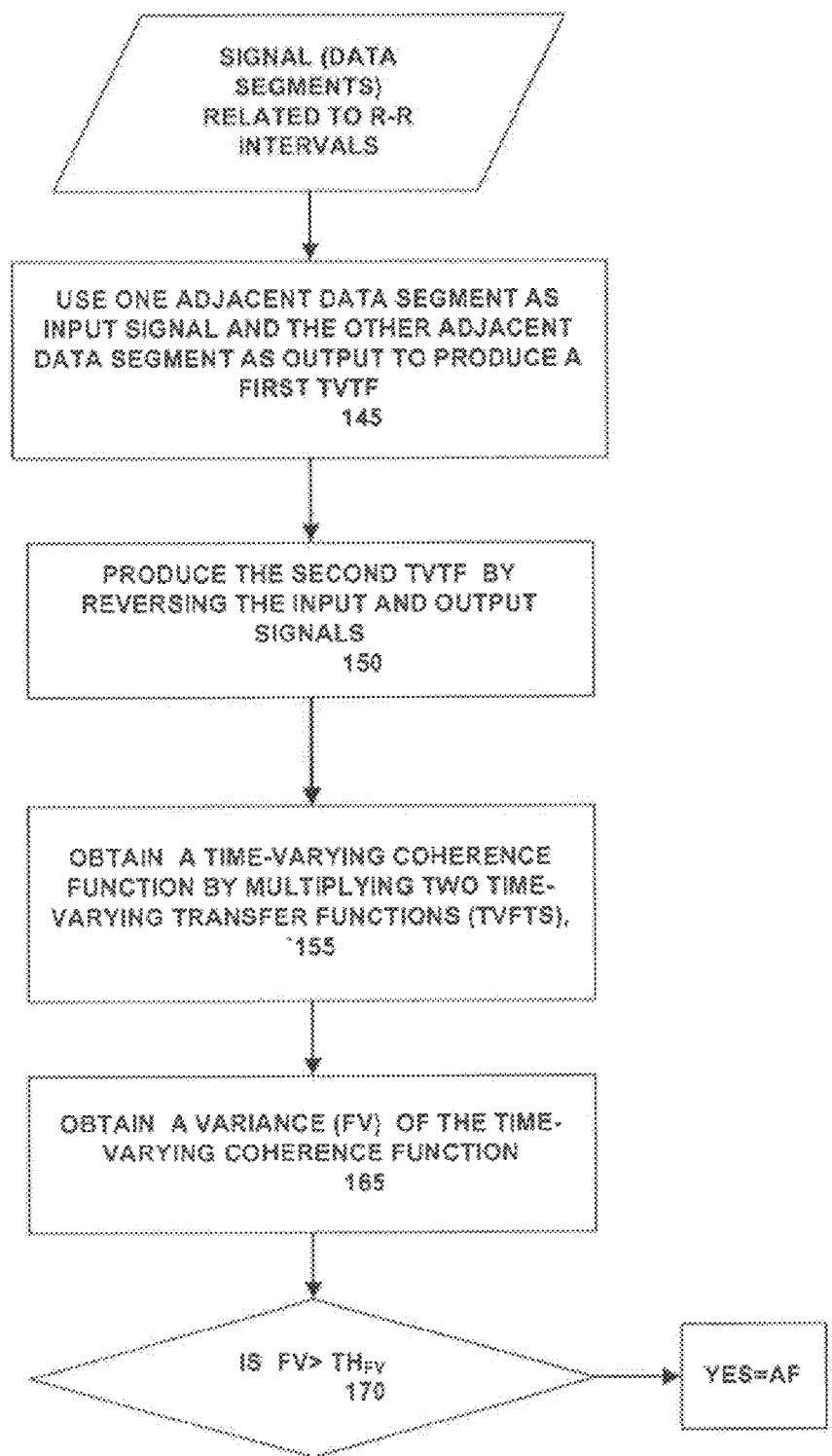
Figure 11:
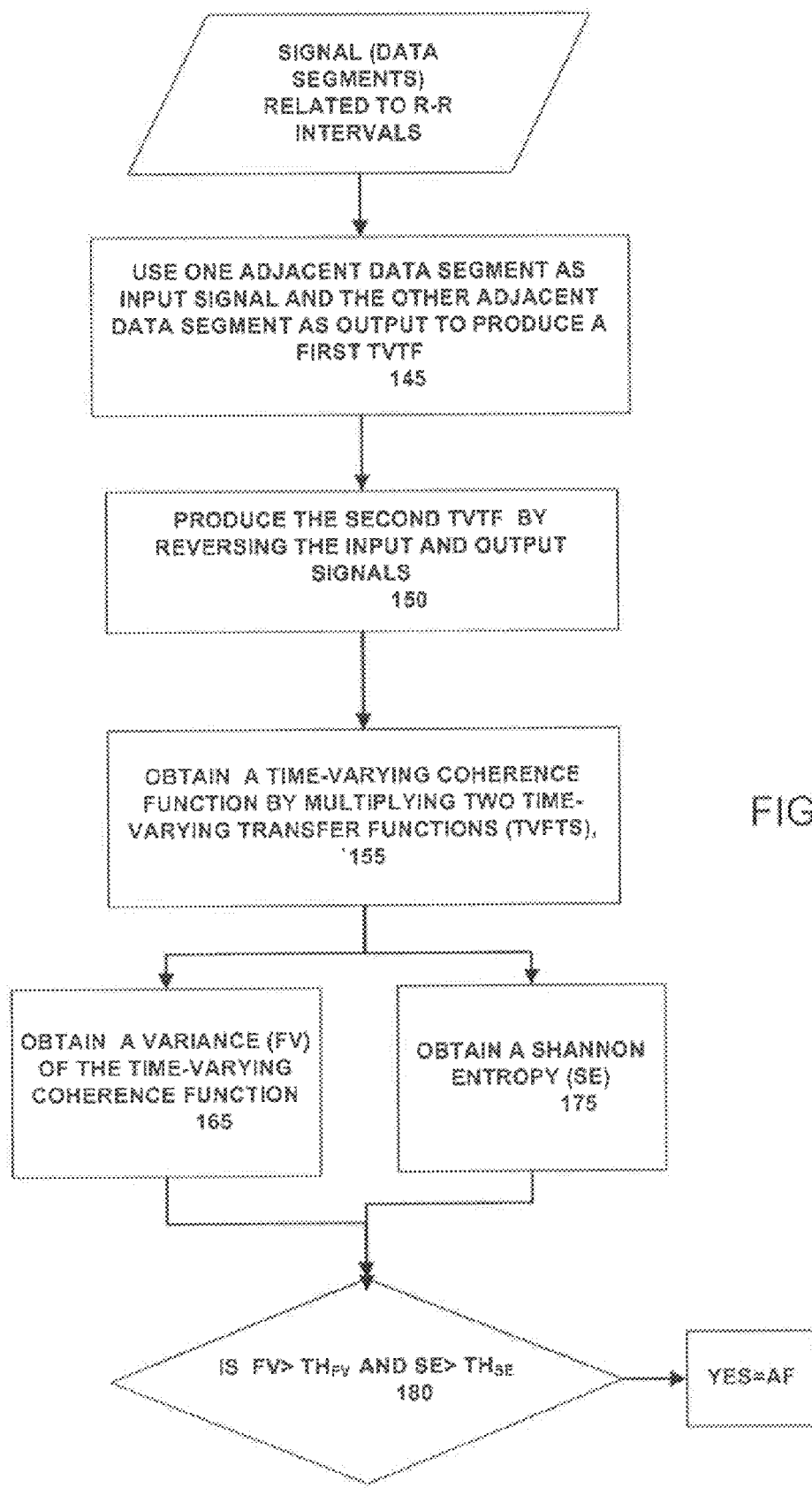

FIGS. 9-11 are flowchart representations of embodiments of the method of these teachings. Steps that are common to several Figures are referred to by the same number in each figure In one or more embodiments of the methods and systems of these teachings for detection of Atrial Fibrillation (AF), the methods and systems use time-varying coherence functions (TVCF) to detect AF. The TVCF is estimated by the multiplication of two time-varying transfer functions (TVTFs) (step 155, FIG. 9). The two TVTFs are obtained using two adjacent data segments, each adjacent data segment being a data segment related to R-R intervals, with one data segment as the input signal and the other data segment as the output to produce the first TVTF (step 145, FIG. 9); the second TVTF is produced by reversing the input and output signals (step 150, FIG. 9). In order to detect AF, it is determined whether the time-varying coherence function (TVCF) is less than a predetermined quantity (step 160, FIG. 9).

In one instance, determining whether the time-varying coherence function is less than the predetermined quantity includes obtaining one or more indicators of atrial fibrillation and determining whether the one or more indicators of atrial fibrillation exceed predetermined thresholds (step 170, FIG. 10; step 180, FIG. 11). In one or more instances, the predetermined thresholds are determined using receiver operator characteristic (ROC) analysis.

In one or more embodiments, the one or more indicators of atrial fibrillation include a variance of the time-varying coherence function (step 165, FIG. 10). In one instance, the one or more indicators of atrial fibrillation also include Shannon entropy (step 175, FIG. 11).

The autoregressive moving average (ARMA) model-based TVCF of these teachings offers higher time and frequency resolutions than do nonparametric approaches. Specifically, an ARMA model-based time-varying transfer function (TVTF) is calculated between two adjacent data segments with one data segment as the input and the other as the output signal. The input and output signals are reversed and the second TVTF is computed, and the two TVTFs to obtain the TVCF are then multiplied (see, for example, H. Zhao, S. Lu, R. Zou et al., "Estimation of time-varying coherence function using time-varying transfer functions," Ann Biomed Eng vol. 33, no. 11, pp. 1582-94, November, 2005, which is incorporated by reference herein in its entirety and for all purposes). the underlying hypothesis for the use of the TVCF approach is that if the two adjacent segments are normal sinus rhythms (NSRs), the resultant TVCF will have values close to one throughout the entire frequency range. However, if either or both segment(s) partially or fully contains AF, the coherence values will dip significantly below one at the time instant AF occurs. Finally, to increase the accuracy of our AF detection, TVCF results are combined with Shannon entropy (SE) were combined, as the latter has been shown to be useful for AF detection.

Methods

A. Databases

Four databases were used to test the method on: the MIT-BIH Atrial Fibrillation (AF), the MIT-BIH normal sinus rhythm (NSR), the MIT-BIH Arrhythmia (Arr) and a 24-hour AF database from The Scottcare Corporation. For all databases, we used RR interval series. The MIT-BIH AF database contains 25 ECG recordings in which there are a total of 299 AF episodes. Each ECG recording is approximately 10 hours in duration. The data sets 4936 and 5091 were excluded from our study due to incorrect AF annotations. The MIT-BIH NSR database contains 18 ECG recordings, and the duration of each ECG data is approximately 24 hours. The NSR data do not contain AF episodes; hence, they were used for evaluation of the specificity value of AF detection. The MIT-BIH Arr database consists of 48 half-hour annotated ECO recordings sampled at 360 Hz; 100 series (n=23) contain both sinus rhythm and arrhythmias without AF episodes while 200 series (n=25) contain AF, various arrhythmias and sinus rhythm. The clinical AF database consists of 24-hour Holter monitor data collected from 15 subjects. All data were collected using ScottCare's RZI53 series recorders. Data were acquired at 180 samples per second with 10 bit resolution. The AF annotation was performed by ScottCare Corporation technicians, and the analysis for R-wave peak detection was done using ScottCare's HolterCare software. The extracted RR intervals were then analyzed using MATLAB 2010a.

B. Time-Varying Coherence Function (TVCF)

The TVCF can be obtained by the multiplication of the two time-varying transfer functions (see, for example, H. Zhao, S. Lu, R. Zou et al., "Estimation of time-varying coherence function using time-varying transfer functions," *Ann Biomed Eng*, vol. 33, no. 11, pp. 1582-94, November, 2005, incorporated by reference herein in its entirety for all purposes). The approach is briefly described hereinbelow. To demonstrate the use of the TVTF in obtaining the TVCF, the TVCF is first defined via the nonparametric time-frequency spectra as $$|\gamma(t,f)|^4 = \frac{|S_{xy}(t,f)|^2}{S_{xx}(t,f)S_{yy}(t,f)} \frac{|S_{yx}(t,f)|^2}{S_{yy}(t,f)S_{xx}(t,f)} \quad (1)$$

where $S_{xy}(t, f)$ and $S_{yx}(t, f)$ represent the time-frequency cross-spectrum, and $S_{xx}(t, f)$ and $S_{yy}(t, f)$ represent the auto spectra of the two signals x and y, respectively. Specifically, the first term in Eq. (1) is the coherence function when x is considered as the input and y as the output. Similarly, the second term in Eq. (1) is the coherence function when y is considered as the input and x as the output. For a linear time varying (TV) system with x as the input and y as the output, the TVTF in terms of time-frequency spectra can be obtained as $$H_{x \to y}(t,f) = \frac{S_{xy}(t,f)}{S_{xx}(t,f)} \quad (2)$$

where $H_{x \to y}(t, f)$ is the TVTF from the input x to the output y signal. Similarly, for a linear TV system with y as the input and x as the output, the TVTF can be obtained as $$H_{y \to x}(t,f) = \frac{S_{yx}(t,f)}{S_{yy}(t,f)} \quad (3)$$

Thus, the time-varying magnitude $|\gamma(t, f)|^2$ is obtained by multiplying the two transfer functions, $$|H_{x \to y}(t,f)H_{y \to x}(t,f)| \quad (4)$$

Given the relationship of (4), a high resolution TVCF can be obtained from ARMA models:

$$y(n) = -\sum_{i=1}^{P_1} a(n,i)y(n-i) + \sum_{j=0}^{Q_1} b(n,j)x(n-j) \quad (5\text{-}1)$$

$$x(n) = -\sum_{i=1}^{P_2} \alpha(n,i)x(n-i) + \sum_{j=0}^{Q_2} \beta(n,j)y(n-j) \quad (5\text{-}2)$$

where (5-1) represents y(n) as the output and x(n) as the input. Similarly, (5-2) represents x(n) as the output and y(n) as the input. Given the ARMA models of (5), the two transfer functions of (4) can be obtained as $$H_{y \to x}(n, e^{jw}) = \frac{B(n, e^{jw})}{A(n, e^{jw})} = \frac{\sum_{i=0}^{Q_1} b(n,j)e^{-jwi}}{1 + \sum_{i=1}^{P_1} a(n,i)e^{-jwi}} \quad (6)$$

$$H_{y \to x}(n, e^{jw}) = \frac{\beta(n, e^{jw})}{\alpha(n, e^{jw})} = \frac{\sum_{i=0}^{Q_2} \beta(n,j)e^{-jwi}}{1 + \sum_{i=1}^{P_2} \alpha(n,i)e^{-jwi}}$$

Finally, we can obtain the TVCF by multiplying the two transfer functions as described in (6). For the parameter estimation, we can use the time-varying optimal parameter search (TVOPS) criterion (see, for example, R. Zou, H. Wang, and K. H. Chon, "A robust time-varying identification algorithm using basis functions," *Ann Biomed Eng*, vol. 31, no. 7, pp. 840-53, July-August, 2003, which is incorporated by reference herein in its entirety for all purposes), which has been shown to be accurate when applied to many diverse physiological signals. For the physiological signals considered, the TVOPS has been shown to be more accurate than the AIC, minimum description length (MDL) and the fast orthogonal search criterion. For TVOPS, time-varying coefficients are expanded onto a set of basis functions. It has been demonstrated that Legendre polynomials are a good choice for capturing dynamics that are smoothly changing with time.

C. New Approach for AF Detection: Variance of TVCF

For AF detection, two adjacent beat segments with the length denoted as seg were formulated using the following ARMA models:

$$S_{i+1:i+seg}(n) = -\sum_{i=1}^{P_1} \alpha(n,i)S_{i+1:i+seg}(n-i) + \quad (7)$$

$$\sum_{j=0}^{Q_2} \beta(n,j)S_{i+seg+1:i+2 \cdot seg}(n-j)$$

$$S_{i+seg+1:i+2 \cdot seg}(n) = -\sum_{i=1}^{P_1} \alpha(n,i)S_{i+seg+2:i+2 \cdot seg}(n-i) +$$

$$\sum_{j=0}^{Q_2} \beta(n,j)S_{i+1:i+seg}(n-j)$$

where $S_{i+1;i+seg}(n)$ and $S_{i+seg+1;i+2 \cdot seg}(n)$ are two adjacent RR interval time series from the $(i+1)^{th}$ to the $(i+seg)^{th}$ and from the $(i+seg+1)^{th}$ to the $(i+2 \cdot seg)^{th}$, respectively. By substituting (7) into (6), the two transfer functions are obtained, and the TVCF is obtained by multiplication of the two TVCFs.

An exemplary embodiment is disclosed hereinbelow. It should be noted that these teachings are not limited only to the exemplary embodiment. The exemplary embodiment is presented to better illustrate these teachings and is not a limitation of this teachings.

In order to illustrate AF detection, the TVCF were calculated using ARMA ($P_1=5$, $Q_1=5$) with the first order Legendre function for subject 8455 of the MIT-BIH AF database. The first order of Legendre polynomials was used since this choice resulted in the best accuracy for the MIT-BIH AF database (N=23). The optimal ARMA model order was found to be $P_1=5$ and $Q_1=5$ with seg=128. A 128 beat segment was used, which was then shifted by 128 beats. A 64 point FFT was used, which resulted in a frequency resolution of 0.0156 Hz. FIG. 1 shows the resultant TVCFs according to each beat and normalized frequency (assuming a Nyquist frequency of 0.5 Hz). As shown in FIG. 1, the TVCF values are close to one throughout the entire frequency range for the two adjacent normal sinus rhythm (NSR) data segments. However, the TVCF values significantly decreased when either or both segments partially or fully contained AF.

Figures 2A, 2B:
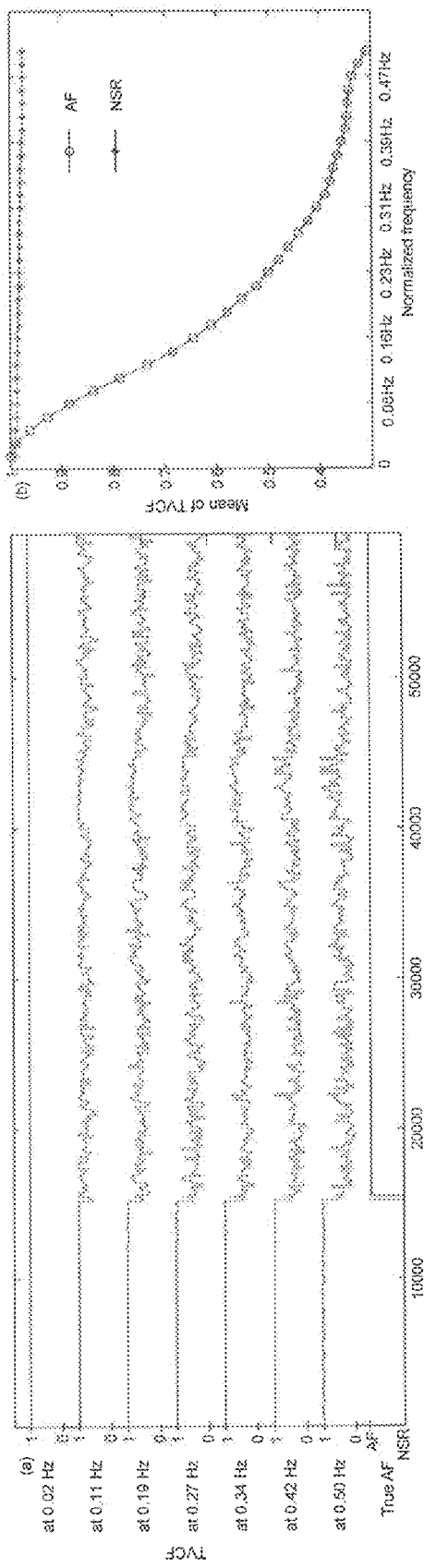
FIGS. 2A and 2B are plots representing TVCF at different frequencies with AF annotation and the mean of the TVCF with AF and NSR according to normalized frequency.

As shown in FIG. 1, it was observed that the TVCF values are highly varying for different frequencies when the patient is in AF. That is, high frequencies tend to have lower coherence values than lower frequencies, in AF (see FIG. 2). To illustrate this phenomenon in more detail, some of the TVCF values selected at various frequencies from FIG. 1 are shown as a function of time in FIG. 2(a). FIG. 2(b) shows the corresponding average values of TVCF according to each normalized frequency and each 128-beat segment for both the AF and NSR databases. It is noted that for AF data, TVCF values start close to one at low frequencies but they drop to low values quickly as the frequency increases. However, for NSR data, the TVCFs are nearly constant (slightly decreasing) at near unit values for all frequencies. This can be explained by the fact that the selected ARMA model terms for AF include largely self and its delay of one lag terms (e.g. x(n), x(n−1), y(n) and y(n−1)), as expected, thus, TVCF values will be high only at the low frequencies and become lower as frequencies increase. Also note in the left panel of FIG. 2a, it is observed that the variance of TVCF values is significantly high for AF but nearly constant for NSR.

Based on the latter observation as described above, in one embodiment, AF is detected by examining the variance of TVCF through the entire frequency range. For each beat, the variance of TVCF values is calculated, termed the frequency variations (FV), among all frequencies. In order to illustrate the method of these teachings, using FV-TVCF, the AF detection performance was examined on the entire MIT-BIH AF database.

Figure 3A:
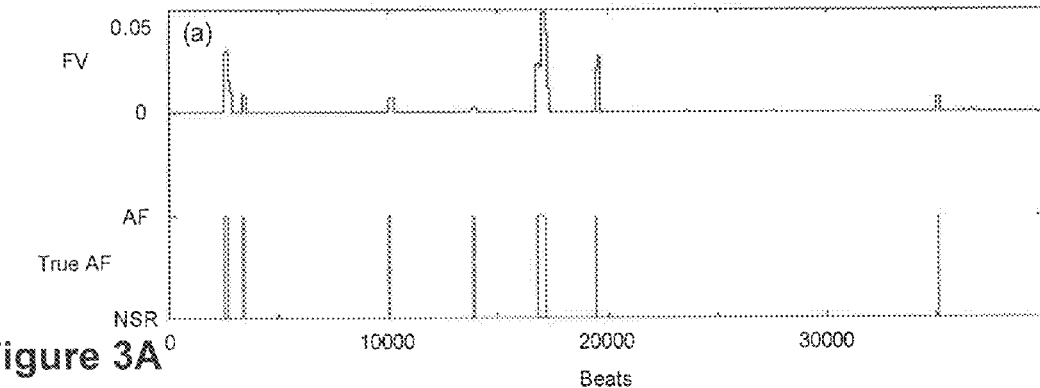
FIGS. 3A-3C illustrate plots of true AF annotation and the values of frequency variations (FV) for (a) MIT-BIH AF 4048, (b) MIT-BIH AF 735, (c) MIT-BIH AF 7162, respectively.
Figure 3B:
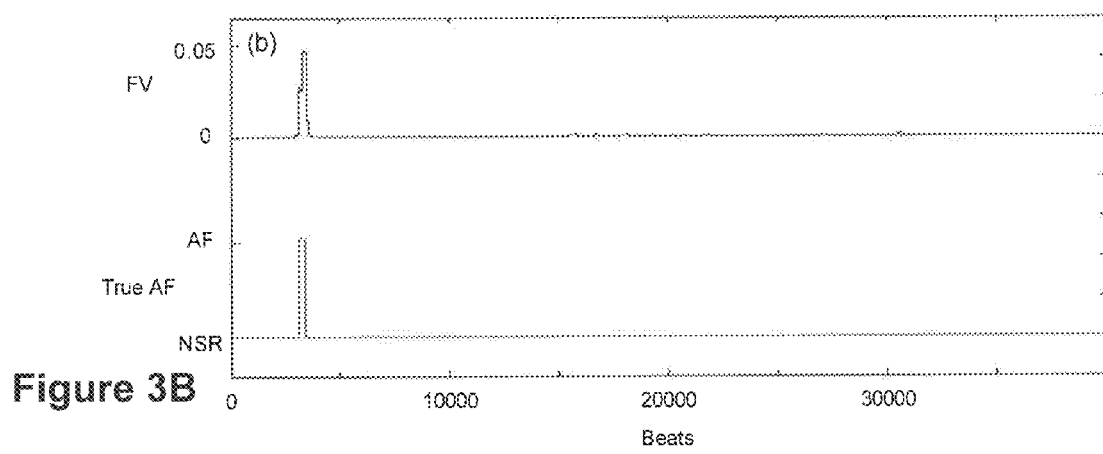
Figure 3C:
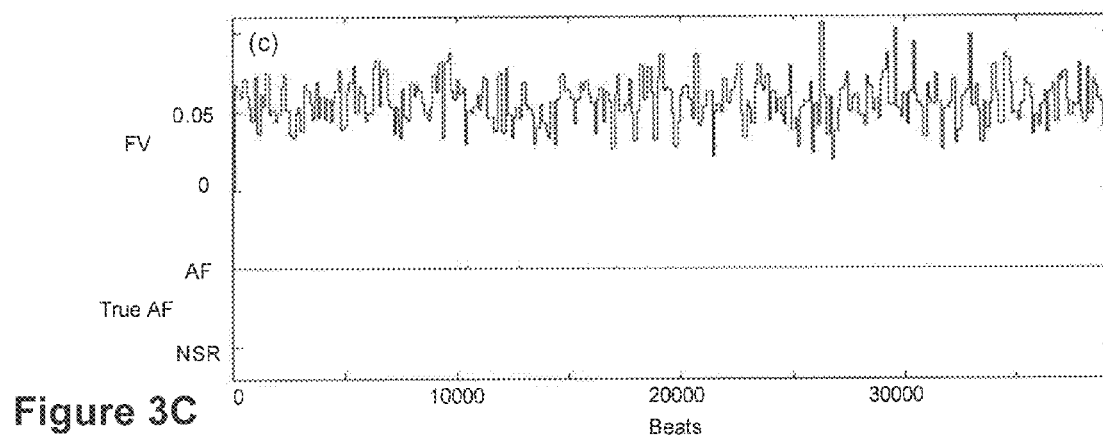

Referring now to FIGS. 3A and 3B, FV-TVCF values and true AF annotation for three representative subjects 4048, 735 and 7162 of the MIT-BIH AF database are shown. In FIG. 3(a), the data set 4048 contains seven AF episodes with lengths of 206, 66, 37, 34, 388, 40 and 42 beats, and the values of FV-TVCF increase in the beats where AF occurs. In FIG. 3(b), the data set 735 contains one AF episode with a length of 332 beats whereas for the dataset 7162, AF episodes persist for the entire time segment shown. The FV-TVCF values reflect this by never returning to a value of zero.

D. Ectopic Beat Elimination and Shannon Entropy Combination

A NSR segment including premature or ectopic beats may also result in lower TVCF values. In order to reduce the effect of the premature and ectopic beats, outliers and filtered ectopic beats were eliminated. To summarize, premature or ectopic beats can be recognized by their signature short-long RR sequence between normal RR intervals. For each RR interval in the time series, the ratio RR(i)/RR(i−1) was computed, where RR(i) is the ith beat, and RR(i) and RR(i+1) were eliminated when the following three conditions were satisfied: 1) RR(i)/RR(i−1)<perc1, 2) RR(i+1)/RR(i)>perc99 and 3) RR(i+1)/RR(i+2)>perc25, where perc1, perc25 and perc99 are the $1^{st}$, $25^{th}$ and $99^{th}$ percentiles based on a histogram of the RR interval values, respectively.

In one embodiment, the Shannon entropy (SE) is also combined with FV-TVCF, to increase the accuracy of AF detection. SE has been shown to be a robust detector of AF (see, for example, S. Dash, K. H. Chon, S. Lu et al, "Automatic real time detection of atrial fibrillation," *Ann Biomed Eng*, vol. 37, no. 9, pp. 1701-9, September, 2009, which is incorporated by reference herein in its entirety and for all purposes) and is estimated according to the following calculation:

$$SE = -\sum_{u=1}^{N_{bin}} p(u) \frac{\log(p(u))}{\log\left(\frac{1}{N_{bin}}\right)} \quad (8)$$

Note that $N_{bin}$ was selected for the best accuracy according to segment lengths while $N_{bin}=16$ was selected.

E. Detector Optimization

In one embodiment, the condition for AF detection can be given by a simple logical AND condition:

If (FV≥$TH_{var}$) AND (SE≥$TH_{SE}$), then classify it as AF.

Else classify it as non-AF $TH_{var}$ and $TH_{SE}$ are the threshold values of the variance and the Shannon entropy, respectively, and are selected based on the best accuracy; specifically, we used receiver operator characteristic (ROC) analyses. For each combination of $TH_{var}$ and $TH_{SE}$, we found the number of True Positives (TP), True Negatives (TN), False Positives (FP) and False Negatives (FN), and used the accuracy (TP+TN)/(TP+TN+FP+FN) on the MIT-BIH AF database. In addition, the sensitivity TP/(TP+FN) and specificity TN/(TN+FP) was calculated. In one instance, the procedure was repeated by changing the order of ARMA model and the lengths of segments. Note that the ARMA model order was restricted by setting $P_1=Q_1$. After finding the values of $TH_{var}$ and $TH_{SE}$ with each different number of model orders and lengths of segments, the same parameters were applied to the databases from MIT-BIH and the clinical AF database.

Results for an exemplary embodiment are disclosed hereinbelow. It should be noted that these teachings are not limited only to the exemplary embodiment. The exemplary embodiment is presented to better illustrate these teachings and is not a limitation of this teachings.

MIT-BIH AF Database

Figure 4A:
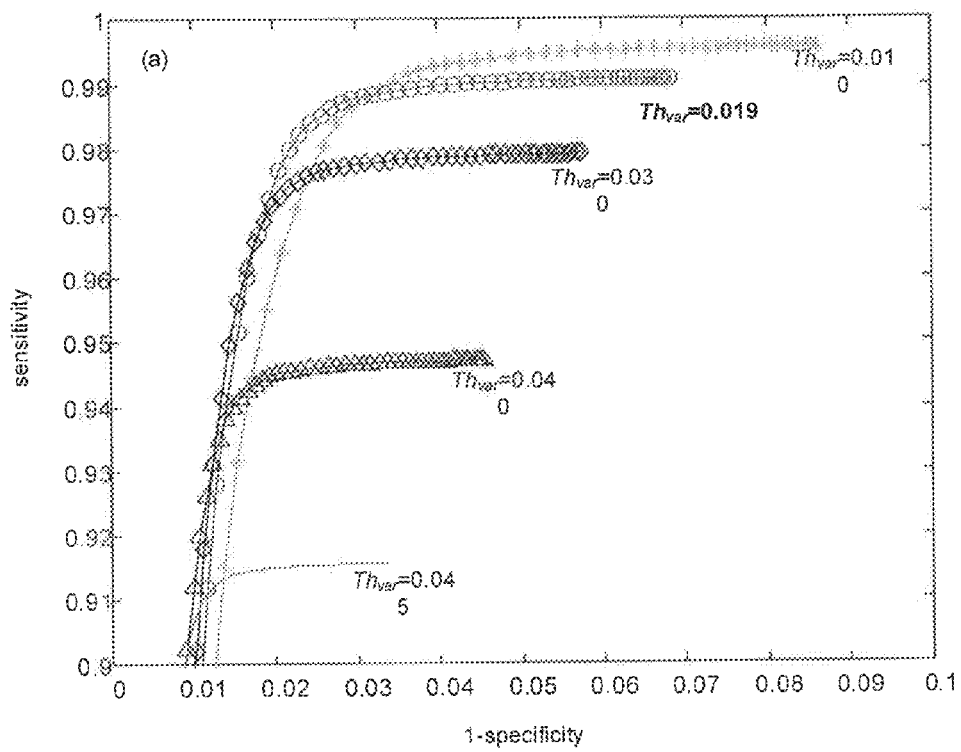
FIGS. 4A-4B illustrate ROC curves (1-specificity vs. sensitivity) by changing $TH_{var}$ and $TH_{SE}$, where seg=128, p=q=5 at (a) $TH_{var}$=0.019 and (b) $TH_{SE}$=0.79, respectively.
Figure 4B:
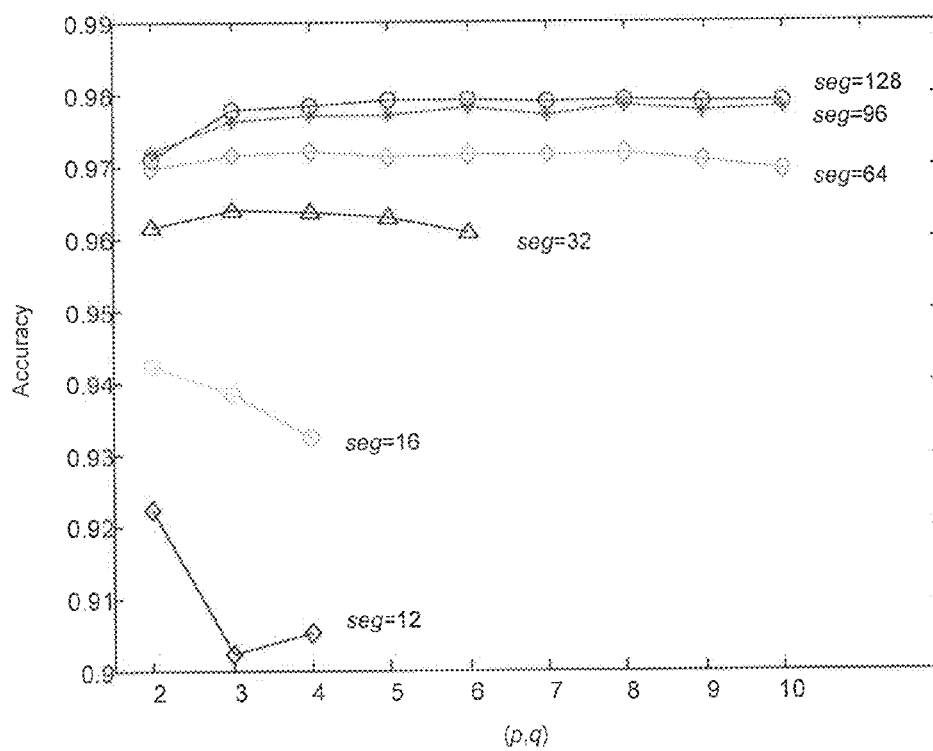
Figure 5:
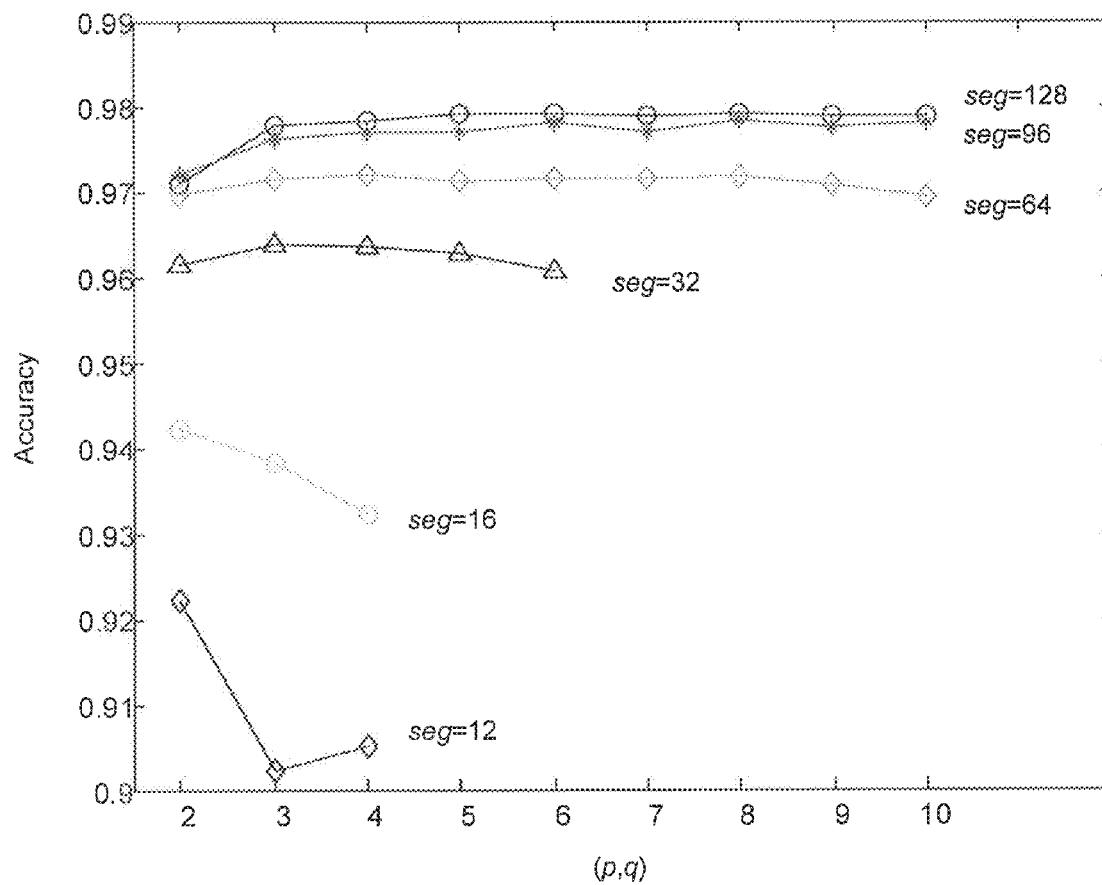
FIG. 5 illustrates a plot representing highest accuracy values according to model and segment length.

The top and bottom panels of FIG. 4 show the ROC curves (1 minus specificity vs. sensitivity) for $TH_{var}$ and $TH_{SE}$, respectively, with seg=128 and $P_1=Q_1=5$. The best accuracy was found to be 0.9791% with $TH_{var}=0.019$ and $T_{SE}=0.79$. In one instance, the procedure was repeated by varying ARMA model orders from (2,2) to (10,10) and segment lengths from 12 to 128; the results are shown in FIG. 5. Seg=128 provided the highest accuracy of all the segment length choices, but its result was not much different than with seg=96. Interestingly, short segment lengths also provided high accuracy values (0.9222 with seg=12 and 0.9421 with seg=16). As for optimal ARMA model order, the accuracies were almost constant for (3,3) to (10,10) when seg=128 or seg=96. On the other hand, when seg=12 or seg=16, the order (2,2) provided the highest accuracy value. The detailed results for seg, ($P_1$, $Q_1$), accuracy, sensitivity, specificity, $TH_{var}$ and $TH_{SE}$ are shown in FIG. 12.

Using these optimal threshold values for seg=128 ($TH_{var}=0.019$, $TH_{SE}=0.79$, (p,q)=(5,5)) and seg=12 ($TH_{var}=0.000076$, $TH_{se}=0.38$, (p,q)=(2,2) and seg=12), the above disclosed method was applied to other databases (e.g., Arr, Holter data and NSR). Short segment AF detection is of interest since 92.2% accuracy using only 12 beats is clinically significant as some of the paroxysmal AF episodes can be as short as 12 beats (ref). Table I shows sensitivity, specificity and accuracy values with SE, FV-TVCF and the combination of FV-TVCF with SE when seg=12 and seg=128. Comparisons to the recently published AF algorithms are presented in Table II. As shown in Table 1, the method of these teachings provides the best accuracy for the MIT-BIH AF database.

TABLE I

COMPARISON OF SENSITIVITY, SPECIFICITY AND ACCURACY ON THE MIT-BIH AF DATABASE; SE, FV-TVCF AND FV-TVCF WITH SE

| | seg = 12 | | | seg = 128 | | |
|---|---|---|---|---|---|---|
| | SE | TVCF | TVCF w/SE | SE | TVCF | TVCF w/SE |
| sensitivity | 0.8285 | 0.9038 | 0.9474 | 0.9568 | 0.9558 | 0.9822 |
| specificity | 0.8639 | 0.9074 | 0.9036 | 0.9398 | 0.9556 | 0.9768 |
| accuracy | 0.8489 | 0.9124 | 0.9222 | 0.9471 | 0.9552 | 0.9791 |

TABLE II

COMPARISON OF RECENT ALGORITHMS ON THE MIT-BIH AF DATABASE AND THE MIT-BIH NSR DATABASE

| | MIT-BIH AF database | |
|---|---|---|
| Methods | sensitivity (%) | specificity (%) |
| TVCF w/ SE | 98.2 | 97.7 |
| Dash et al. [8] | 94.4 | 95.1 |
| Tateno el al. [11] | 94.4 | 97.2 |
| Huang et al. [12] | 96.1 | 98.1 |
| Logan el al. [10] | 96.0 | 89.0 |
| Kikillus et al. [9] | 94.4 | 93.4 |

Figure 6:
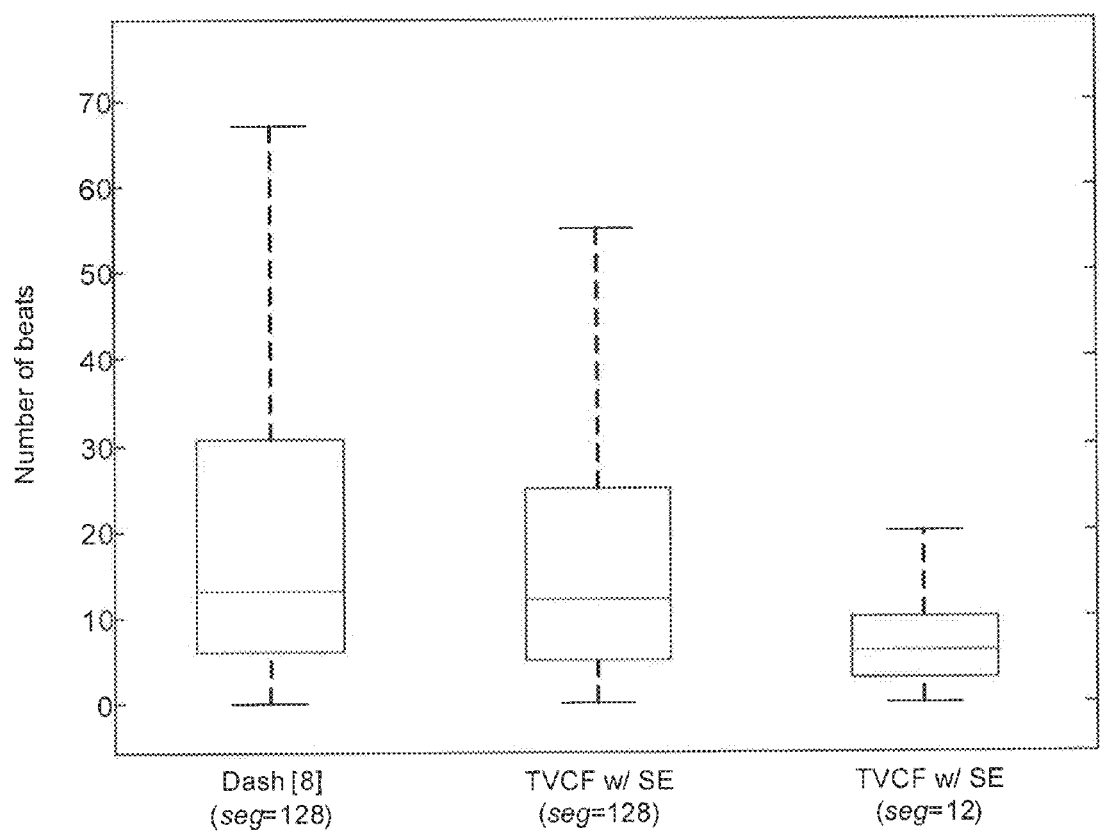
FIG. 6 is a chart illustrating a comparison of transition delay (beats)

Clinically, it is important to detect the presence of AF episodes in a given segment, not necessarily in every beat. Using this criterion on the MIT-BIH AF database (excluding files 4936 and 5091), the total number of true AF episodes is 255 and the method of these teachings with either seg=12 or seg=128 beats correctly detected the presence of all AF episodes. This result outperforms other recently-published algorithms: showing 88.2% and 89.3% AF episode detection rate. In addition, an embodiment of the method of these teachings provides one of the fastest transition times (e.g., AF to NSR or/and NSR to AF). FIG. 6 compares the transition time (delay beats). The median of the transition delay with seg=12 is only 6 beats, which also outperforms any other recently-published algorithm: showing 18 beats and 70 beats.

Figure 7:
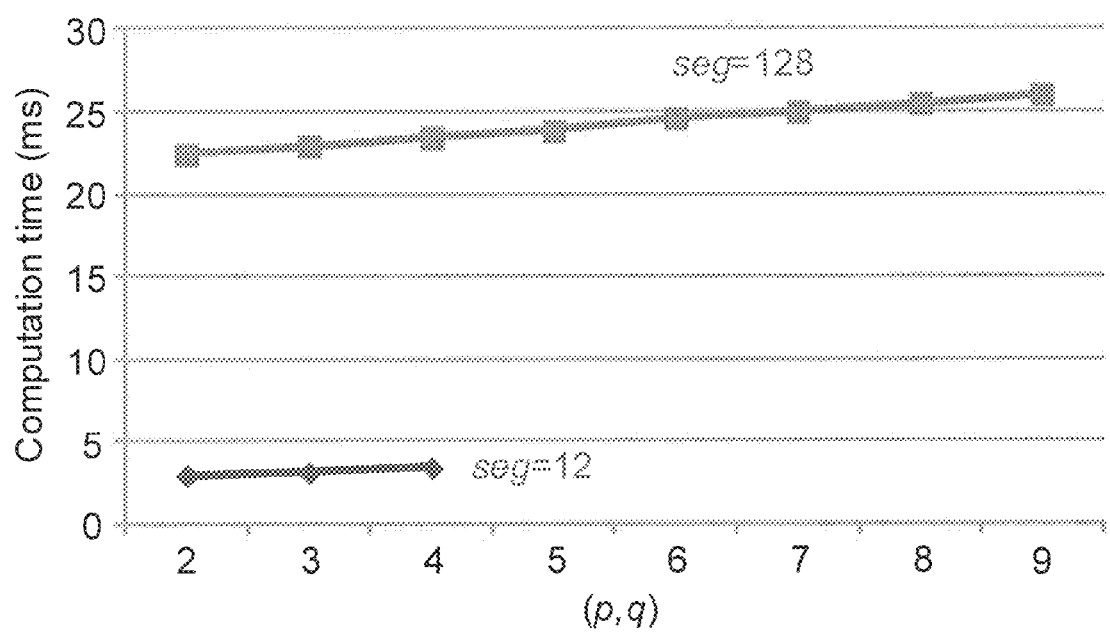
FIG. 7 is a plot illustrating computation time according to seg and (p,q)

FIG. 7 shows, for one embodiment of the method and system of these teachings, the computation time according to seg and (p,q), where the computation time is between 20 and 30 milliseconds (ms) with seg=128, and between 3 and 4 ms with seg=$1^2$ (programs run in MATLAB 2010a on 2.66 GHz Intel Core2 processor). This shows that the exemplary embodiment of the method of these teachings can be realizable in real time for practical applications, and it is faster than other algorithms (compare to 5.2 seconds with seg=128 in D. E. Lake, and J. R. Moorman, "Accurate estimation of entropy in very short physiological time series: the problem of atrial fibrillation detection in implanted ventricular devices," *Am J Physiol Heart Circ Physiol*, vol. 300, no. 1, pp. H319-25, January, 2011, 200 ms with seg=128 in S. Dash, K. H. Chon, S. Lu et al., "Automatic real time detection of atrial fibrillation," *Ann Biomed Eng*, vol. 37, no. 9, pp. 1701-9, September, 2009 (herinafter "Dash"), and 3 s with seg=100 in K. Tateno, and L. Glass, "Automatic detection of atrial fibrillation using the coefficient of variation and density histograms of RR and deltaRR intervals," *Med Biol Eng Comput*, vol. 39, no. 6, pp. 664-71, November, 2001, using. MIT-BIH NSR Database, MIT-BIH Art Database and Clinical AF Database).

The substantially optimal parameters mentioned above with seg=12 and seg=128 were applied to the MIT-BIH NSR database, MIT-BIH Arr Database and Clinical AF Database. For the MIT-BIH NSR database the specificity was 94.37% with seg=12 and 100% with seg=128, which compares favorably to other published results: 99.7% with seg=128 in Dash, 97.9% with seg=100 in C. Huang, S. Ye, H. Chen et al., "A novel method for detection of the transition between atrial fibrillation and sinus rhythm," *IEEE Trans Biomed Eng*, vol. 58, no. 4, pp. 1113-9, April, 2011 and 96.9% with seg=500 in N. Kikillus, G. Hammer, N. Lentz et al., "Three different algorithms for identifying patients suffering from atrial fibrillation during atrial fibrillation free phases of the ECG," *Comput. Cardiol.*, vol. 34, pp. 801-804, 2007. For the 100 series MIT-BIH Arr database, the specificity was 91.8% with seg=12 and 99.7% with seg=128, whereas it was 99.5% in Dash with seg=128. Note that the 100 series contains no true AF beats. For the 200 series MIT-BIH Arr database, the sensitivity and specificity were 92.4% and 76.5% with seg=12, and 91.1% and 89.7% with seg=$1^{28}$ which compares well with 90.2% and 91.2% in Dash using seg=128. In the 200 series MIT-BIH Art database, the total number of true AF episodes is 79, and the exemplary embodiment of the method of these teachings with seg=12 correctly detected 73 AF episodes (92.4%) which is better than the 73.4% in Dash. For the clinical AF database, the sensitivity and specificity were 93.7% and 83.9% with seg=12, and 91.5% and 93.7% with seg=128.

In summary, it was found that the resultant TVCF between two adjacent normal sinus rhythm segments show high coherence values (near 1) throughout the entire frequency range. However, if either or both segments partially or fully contain AF, the resultant TVCF is significantly lower than 1. When TVCF was combined with Shannon entropy (SE), even more accurate AF detection rate of 97.9% were obtained for the MIT-BIH Atrial Fibrillation (AF) database (n=23) with 128 beat segments. The exemplary embodiment of the method of these teachings was tested on four databases using 128 beat segments: the MIT-BIH AF database, the MIT-BIH normal sinus rhythm (NSR) database (n=18), the MIT-BIH Arrhythmia database (n=48), and a clinical 24-hour Holter AF database (n=15).

Using the receiver operating characteristic curves from the combination of TVCF and SE, for the exemplary embodiment of the method of these teachings, a sensitivity of 98.2% and specificity of 97.7% were obtained for the MIT-BIH AF database. For the MIT-BIH NSR database, a specificity of 99.7% was found. For the MIT-BIH Arrhythmia database, the sensitivity and specificity were 91.1% and 89.7%, respectively. For the clinical database (24-hour Holter data), the sensitivity and specificity were 91.5% and 93.7%, respectively. It was also found that a short segment (12 beats) also provided accurate AF detection for all databases: sensitivity of 94.7% and specificity of 90.4% for the MIT-BIH AF, specificity of 94.4% for the MIT-BIH-NSR, the sensitivity of 92.4% and specificity of 84.1% for the MIT-BIH Arrhythmia, and sensitivity of 93.7% and specificity of 83.9% for the clinical database. The advantage of using a short segment is more accurate AF burden calculation as the timing of transitions between normal sinus rhythm and AF are more accurately detected.

Results for an exemplary embodiment of the system of these teachings have been presented here in above. In one or more embodiments, the system of these teachings includes an analysis component analyzing a signal related to R-R intervals; the analysis component obtaining a time-varying coherence function by multiplying two time-varying transfer functions (TVFTs), the two time-varying transfer functions obtained using two adjacent data segments, each adjacent data segment being a data segment related to R-R intervals, with one data segment as input signal and the other data segment as output to produce the first TVTF; the second TVTF is produced by reversing the input and output signals, using said other data segment as input signal and said one data segment as output; and determining whether the time-varying coherence function is less than a predetermined quantity.

Figure 8:
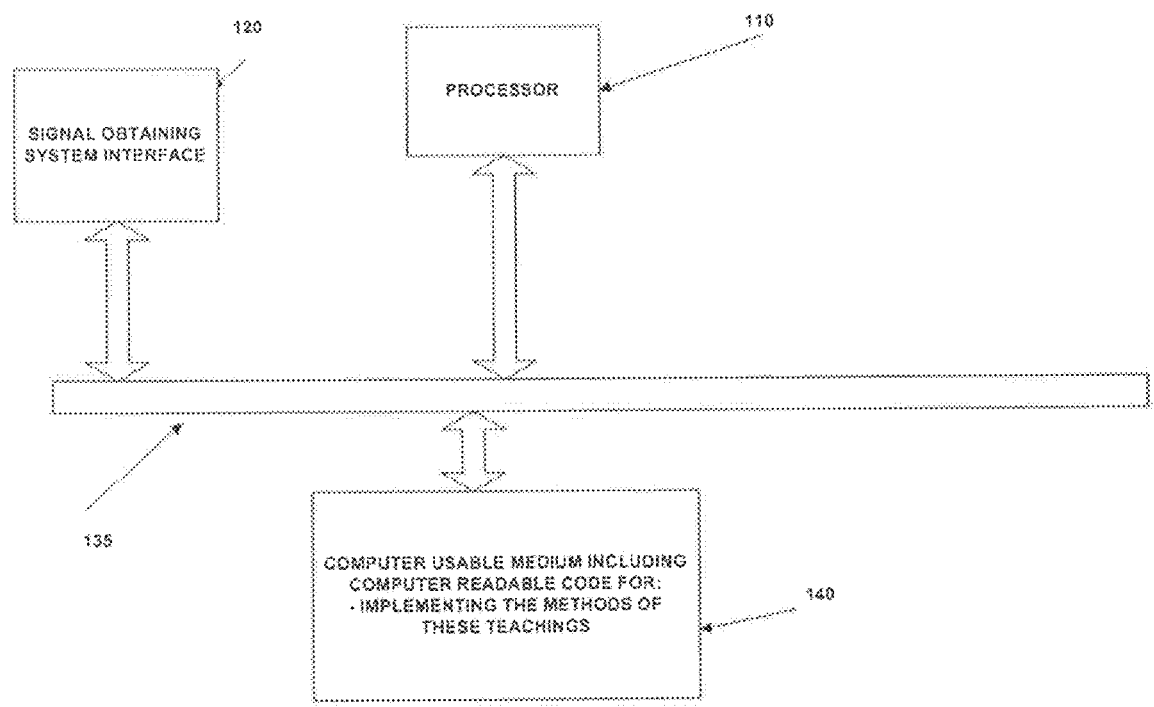
FIG. 8 is a block diagram representation of one embodiment of the system of these teachings.

The analysis component can be, in one instance, a dedicated component such as an application-specific circuit (ASIC) or a circuit including an FPGA (field programmable gate array) or similar. In another instance, the analysis component includes one or more processors and one or more computer usable media having computer readable code embodied therein, the computer readable code causing the one or more processors to obtain a time-varying coherence function by multiplying two time-varying transfer functions (TVFTs), the two time-varying transfer functions obtained using two adjacent data segments, each adjacent data segment being a data segment related to R-R intervals, with one data segment as input signal and the other data segment as output to produce the first TVTF, the second TVTF being produced by reversing the input and output signals and determine whether the time-varying coherence function is less than a predetermined quantity, FIG. 8 shows a block diagram of an embodiment of the system of these teachings. Referring to FIG. 8, in the embodiment shown there in, the system includes an interface 120 to a signal obtaining subsystem, the signal obtaining subsystem providing the signal related to R-R intervals, one or more processors 110 and computer readable media 140 having a computer readable code, the computer readable code causing the processor to implement the method of these teachings. The interface 120, the one or more processors 110 and the computer readable media 140 are operatively connected by a connection component 135 (such as, but not limited to, a computer bus).

The method and system of these teachings is applicable for a Holter system as it is real-time realizable. The computation time was approximately 3-4 ms with seg=12 and 20-30 ms with seg=128 running Matlab 2010a on a 2.80 GHz Intel Core2 processor. Real-time realizable capability is important not only for Holter monitoring, but also for AF detection using a Mobile device, such as, but not limited to, a smart phone (see, for example, WIPO (PCT) Published Application WO 2012/100175, corresponding to WIPO (PCT) Patent Application PCT/US2012/022049, entitled PHYSIOLOGICAL PARAMETER MONITORING WITH A MOBILE COMMUNICATION DEVICE, filed Jan. 20, 2012, and C. Scully, J. Lee, J. Meyer et al., "Physiological Parameter Monitoring from Optical Recordings with a Mobile Phone," *IEEE Trans Biomed Eng*, Jul. 29, 2011, all of which are incorporated by reference herein in their entirety and for all purposes.) In C. Scully, J. Lee, J. Meyer et al., "Physiological Parameter Monitoring from Optical Recordings with a Mobile Phone," *IEEE Trans Biomed Eng*, Jul. 29, 2011, and in WIPO (PCT) Patent Application PCT/US2012/022049, it has been shown that RR interval data can be derived from a video camera that resides in a smart phone or similar mobile device. Given this new capability, AF detection is possible using a Mobile device, such as, but not limited to, a smart phone and the need for a real-time detection AF algorithm becomes even more evident.

When used with a mobile device, motion and noise artifacts can be detected using method such as, but not limited to, those disclosed in WIPO (PCT Published Application WO 2012/051320, corresponding to WIPO (PCT) International Application Number PCT/US11/55989, filed on Oct. 12, 2011, entitled MOTION AND NOISE ARTIFACT DETECTION FOR ECO DATA, both of which are incorporated by reference herein in their entirety and for all purposes.

As disclosed herein, an AF detection method is disclosed by using an ARMA model based approach to calculate the TVCF. While not desiring to be bound by theory, the rationale for using the TVCF is twofold. First, AF dynamics are known to be highly random, thus, the coherence function should be significantly lower than for normal sinus rhythm. Second, especially for a person who has paroxysmal AF, AF dynamics are not only non-stationary, they transition frequently between normal sinus rhythm and AF. While Sarraf et al. have previously used a time-invariant coherence function approach to discriminate between AF and non-AF rhythms and to account for nonstationary dynamics of AF as well as to capture transitions from AF to sinus rhythms, the ARMA based TVCF of these teachings results in higher time and frequency resolutions than do nonparametric approaches. Lovett and Ropella have used a spectrogram approach. However, the Lovett and Ropella study was not intended for AF detection. Further, because the spectrogram does not provide the best time- and frequency-resolution, its ability to find the transition between AF and normal sinus rhythms is not optimal.

Further, because the spectrogram does not provide the best time- and frequency-resolution, its ability to find the transition between AF and normal sinus rhythms is not as optimal as that of the high-resolution ARMA model based TVCF of these teachings. The dominant AF frequency has been known to be time-varying, thus, the use of TVCF in these teachings is warranted. The accuracy of the TVCF in these teachings depends on the level of broadband characteristics of the signals. Certainly, AF which has random dynamics is well suited for the estimation of TVCF using the method of these teachings. Note also that normal sinus rhythm has sufficiently broadband characteristics to be well suited for estimation by TVCF.

Using the TVCF approach of these teachings, the accuracy values with seg=128 were 97.9%, 100%, 94.3% and 92.2% on the MIT-BIH AF, the MIT-BIH NSR, the MIT-BIH Arr and clinical databases, respectively. While these accuracy values are noteworthy, the most attractive feature of the TVCF is that it can be used to accurately find AF onset and the transition to NSR since the method of these teachings provides good accuracy even with short data segments (seg=12). This is important in order to accurately calculate AF burden, a measure of the percent of time a patient spends in AF.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Elements and components described herein may be further divided into additional components or joined together to form fewer components for performing the same functions.

Each computer program may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable media include, for example, a floppy disk, a flexible disk, hard disk, magnetic tape, or any other magnetic medium, a CDROM, any other optical medium, any physical medium with patterns of holes, a RAM, a PROM, and EPROM, a FLASH-EPROM, any other memory chip or cartridge, all of which are non-transitory. As stated in the USPTO 2005 Interim Guidelines for Examination of Patent Applications for Patent Subject Matter Eligibility, 1300 Off. Gaz. Pat. Office 142 (Nov. 22, 2005), "On the other hand, from a technological standpoint, a signal encoded with functional descriptive material is similar to a computer-readable memory encoded with functional descriptive material, in that they both create a functional interrelationship with a computer. In other words, a computer is able to execute the encoded functions, regardless of whether the format is a disk or a signal."

The present disclosure is illustratively described above in reference to the disclosed embodiments. Various modifications and changes may be made to the disclosed embodiments by persons skilled in the art without departing from the scope of the present disclosure.

What is claimed is:

1. A processor implemented method for detecting atrial fibrillation, the processor implemented method comprising:
   obtaining, using one or more processors executing computer readable code embodied in computer usable media, a time-varying coherence function by multiplying two time-varying transfer functions (TVFTs), the two time-varying transfer functions obtained using two adjacent data segments, each of the two adjacent data segment being related to R-R intervals, with one of the two adjacent data segment as an input signal and another of the two adjacent data segment as an output signal to produce a first TVTF; a second TVTF is produced by reversing the input and the output signals, using said another of the two adjacent data segment as the input signal and said one of the two adjacent data segment as the output signal; and
   determining, using the one or more processors executing the computer readable code embodied in the computer usable media, whether the time-varying coherence function is less than a predetermined quantity.

2. A processor implemented method for detecting atrial fibrillation, the processor implemented method comprising:
   obtaining, using one or more processors executing computer readable code embodied in computer usable media, a time-varying coherence function by multiplying two time-varying transfer functions (TVFTs), the two time-varying transfer functions obtained using two adjacent data segments, each of the two adjacent data segment being related to R-R intervals, with one of the two adjacent data segment as an input signal and another of the two adjacent data segment as an output signal to produce a first TVTF; a second TVTF is produced by reversing the input and the output signals, using said another of the two adjacent data segment as the input signal and said one of the two adjacent data segment as the output signal; and
   determining, using the one or more processors executing the computer readable code embodied in the computer usable media, whether the time-varying coherence function is less than a predetermined quantity; wherein determining whether the time-varying coherence function is less than the predetermined quantity comprises:
   obtaining one or more indicators of atrial fibrillation; and
   determining whether the one or more indicators of atrial fibrillation exceed predetermined thresholds.

3. The method of claim 2 wherein the one or more indicators of atrial fibrillation comprise a variance of the time-varying coherence function.

4. The method of claim 3 wherein the one or more indicators of atrial fibrillation also comprise Shannon entropy.

5. The method of claim 2 wherein the predetermined thresholds are determined using receiver operator characteristic (ROC) analysis.

6. A system for detecting atrial fibrillation, the system comprising: an analysis component configured to analyze a signal related to R-R intervals; the analysis component being also configured to obtain a time-varying coherence function by multiplying two time-varying transfer functions (TVFTs), the two time-varying transfer functions obtained using two adjacent data segments, each of the two adjacent data segment being related to R-R intervals, with one of the two adjacent data segment as an input signal and another of the two adjacent data segment as an output signal to produce a first TVTF; a second TVTF being produced by reversing input and output signals, using said another of the two adjacent data segment as the input signal and said one of the two adjacent data segment as the output; the analysis component being also configured to determine whether the time-varying coherence function is less than a predetermined quantity.

7. A system for detecting atrial fibrillation, the system comprising:
   an analysis component configured for analyzing a signal related to R-R intervals; the analysis component being also configured for obtaining a time-varying coherence function by multiplying two time-varying transfer functions (TVFTs), the two time-varying transfer functions obtained using two adjacent data segments, each of the two adjacent data segment being related to R-R intervals, with one of the two adjacent data segment as an input signal and another of the two adjacent data segment as an output to produce a first TVTF; a second TVTF being produced by reversing input and output signals, using said another of the two adjacent data segment as the input signal and said one of the two adjacent data segment as the output; the analysis component being also configured for determining whether the time-varying coherence function is less than a predetermined quantity; wherein the analysis component comprises:
   at least one processor; and
   at least one computer usable medium, the computer usable medium having computer readable code embodied therein, the computer readable code causing the at least one processor to:
   obtain a time-varying coherence function by multiplying two time-varying transfer functions (TVFTs), the two time-varying transfer functions obtained using two adjacent data segments, each of the two adjacent data segment being related to R-R intervals, with one of the two adjacent data segment as an input signal and another of the two adjacent data segment as an output signal to produce the first TVTF; the second TVTF being produced by reversing the input and output signals; and
   determine whether the time-varying coherence function is less than a predetermined quantity.

8. The system of claim 7 wherein the computer readable code, in causing the at least one processor to determine whether the time-varying coherence function is less than the predetermined quantity, causes the at least one processor to:
  obtain one or more indicators of atrial fibrillation; and
  determine whether the one or more indicators of atrial fibrillation exceed predetermined thresholds.

9. The system of claim 8 wherein the one or more indicators of atrial fibrillation comprise a variance of the time-varying coherence function.

10. The system of claim 9 wherein the one or more indicators of atrial fibrillation also comprise Shannon entropy.

11. The system of claim 8 wherein the predetermined thresholds are determined using receiver operator characteristic (ROC) analysis.

12. A non-transitory computer usable medium having computer readable code embodied therein, the computer readable code causing at least one processor to:
  analyze a signal related to R-R intervals in order to detect atrial fibrillation; wherein the computer readable code, in causing the at least one processor to analyze a signal related to R-R intervals, causes the at least one processor to:
    obtain a time-varying coherence function by multiplying two time-varying transfer functions (TVFTs), the two time-varying transfer functions obtained using two adjacent data segments with one of the two adjacent data segment as an input signal and another of the two adjacent data segment as an output signal to produce a first TVTF; a second TVTF is produced by reversing the input and output signals; and
    determine whether the time-varying coherence function is less than a predetermined quantity.

13. A non-transitory computer usable medium having computer readable code embodied therein, the computer readable code causing at least one processor to:
  analyze a signal related to R-R intervals in order to detect atrial fibrillation; wherein the computer readable code, in causing the at least one processor to analyze a signal related to R-R intervals, causes the at least one processor to:
    obtain a time-varying coherence function by multiplying two time-varying transfer functions (TVFTs), the two time-varying transfer functions obtained using two adjacent data segments with one of the two adjacent data segment as an input signal and another of the two adjacent data segment as an output signal to produce a first TVTF; a second TVTF is produced by reversing the input and output signals; and
    determine whether the time-varying coherence function is less than a predetermined quantity;
  wherein the computer readable code, in causing the at least one processor to determine whether the time-varying coherence function is less than the predetermined quantity, causes the at least one processor to:
    obtain one or more indicators of atrial fibrillation;
    determine whether the one or more indicators of atrial fibrillation exceed predetermined thresholds.

14. The non-transitory computer usable medium of claim 13 wherein the one or more indicators of atrial fibrillation comprise a variance of the time-varying coherence function.

15. The non-transitory computer usable medium of claim 14 wherein the one or more indicators of atrial fibrillation also comprise Shannon entropy.

16. The non-transitory computer usable medium of claim 13 wherein the predetermined thresholds are determined using receiver operator characteristic (ROC) analysis.

* * * * *

UNITED STATES PATENT AND TRADEMARK OFFICE
CERTIFICATE OF CORRECTION

PATENT NO.        : 8,755,876 B2                                     Page 1 of 1
APPLICATION NO.   : 13/684979
DATED             : June 17, 2014
INVENTOR(S)       : Chon et al.

It is certified that error appears in the above-identified patent and that said Letters Patent is hereby corrected as shown below:

In the Claims
Column 14, line 28 claim 6, "as the output;" should read -- as the output signal; --
Column 14, line 42 claim 7, "as an output" should read -- as an output signal --
Column 14, line 46 claim 7, "as the output;" should read -- as the output signal; --

Signed and Sealed this
Twenty-third Day of September, 2014

Michelle K. Lee
*Deputy Director of the United States Patent and Trademark Office*